US012781236B2

(12) United States Patent
Liu et al.

(10) Patent No.: US 12,781,236 B2
(45) Date of Patent: Nov. 3, 2026

(54) miRNA RELATED TO RESISTANCE AND LEAF EPICUTICULAR WAX CONTENT OF CITRUS PLANT AND USE THEREOF

(71) Applicant: Jiangxi Agricultural University, Nanchang City (CN)

(72) Inventors: Dechun Liu, Nanchang City (CN); Yong Liu, Nanchang City (CN); Jingheng Xie, Nanchang City (CN); Li Yang, Nanchang City (CN); Wei Hu, Nanchang City (CN); Jie Song, Nanchang City (CN); Liuqing Kuang, Nanchang City (CN)

(73) Assignee: JIANGXI AGRICULTURAL UNIVERSITY, Nanchang City (CN)

( * ) Notice: Subject to any disclaimer, the term of this patent is extended or adjusted under 35 U.S.C. 154(b) by 46 days.

(21) Appl. No.: 19/023,909

(22) Filed: Jan. 16, 2025

(65) Prior Publication Data

US 2025/0354162 A1 Nov. 20, 2025

(30) Foreign Application Priority Data

May 14, 2024 (CN) ......................... 202410593737.2

(51) Int. Cl.
*C12N 15/82* (2006.01)

(52) U.S. Cl.
CPC ..... *C12N 15/8205* (2013.01); *C12N 15/8218* (2013.01); *C12N 15/8273* (2013.01)

(58) Field of Classification Search
CPC ............ C12N 15/8205; C12N 15/8218; C12N 15/8273
See application file for complete search history.

(56) References Cited

U.S. PATENT DOCUMENTS

2019/0161766 A1* 5/2019 Dhankher .......... C12N 15/8273

FOREIGN PATENT DOCUMENTS

CN 112322623 A * 2/2021 ......... C12N 15/8218

OTHER PUBLICATIONS

Xie, Jingheng, et al. "The CsMYB44-csi-miR0008-CsCER1 module regulates cuticular wax biosynthesis and drought tolerance in citrus." New Phytologist 246.4 (2025): 1757-1779.*

Tang, Guiliang, et al. "Construction of short tandem target mimic (STTM) to block the functions of plant and animal microRNAs." Methods 58.2 (2012): 118-125.*

Wang, Rong, et al. "The miR399-CsUBC24 module regulates reproductive development and male fertility in citrus." Plant Physiology 183.4 (2020): 1681-1695.*

Li, Rong-Jun, et al. "Diurnal regulation of plant epidermal wax synthesis through antagonistic roles of the transcription factors SPL9 and DEWAX." The Plant Cell 31.11 (2019): 2711-2733.*

Dominguez, Michelle M., Carmen S. Padilla, and Kranthi K. Mandadi. "A versatile Agrobacterium-based plant transformation system for genetic engineering of diverse citrus cultivars." Frontiers in Plant Science 13 (2022): 878335.*

Arief, M. A. A., Kim, H., Kurniawan, H., Nugroho, A. P., Kim, T., & Cho, B. K. (Mar. 21, 2023). Chlorophyll fluorescence imaging for early detection of drought and heat stress in strawberry plants. Plants, 12(6), 1387.

* cited by examiner

*Primary Examiner* — Bratislav Stankovic
*Assistant Examiner* — George W Meyer
(74) *Attorney, Agent, or Firm* — Tutunjian & Bitetto, P.C.

(57) ABSTRACT

An miRNA related to resistance and a leaf epicuticular wax content of a *Citrus* plant and use thereof are provided, relating to the technical field of genetic engineering. An miRNA related to resistance and a leaf epicuticular wax content of a *Citrus* plant is provided, where the miRNA is named csi-miRn0008, with a mature sequence shown in SEQ ID NO: 1. A DNA molecule encoding a precursor sequence of the csi-miRn0008 is used to obtain a csi-miRn0008 silencing expression vector through the short tandem target mimic (STTM) technology, and then the vector is introduced into a target plant, thus effectively regulating leaf epicuticular wax content, drought resistance, and salt resistance of the *Citrus* plant. Provided enriches existing research results in the field of miRNAs and lays a theoretical foundation and provides high-quality gene resources for breeding novel *citrus* stress-resistant varieties.

2 Claims, 12 Drawing Sheets

Specification includes a Sequence Listing.

miRNA RELATED TO RESISTANCE AND LEAF EPICUTICULAR WAX CONTENT OF CITRUS PLANT AND USE THEREOF

CROSS REFERENCE TO RELATED APPLICATION

This patent application claims the benefit and priority of Chinese Patent Application No. 2024105937372 filed with the China National Intellectual Property Administration on May 14, 2024, the disclosure of which is incorporated by reference herein in its entirety as part of the present application.

REFERENCE TO SEQUENCE LISTING

A computer readable XML file entitled "GWP20241107238", that was created on Dec. 26, 2024 with a file size of about 23,070 bytes, contains the sequence listing for this application, has been filed with this application, and is hereby incorporated by reference in its entirety.

TECHNICAL FIELD

The present disclosure belongs to the technical field of genetic engineering, and specifically relates to an miRNA related to resistance and a leaf epicuticular wax content of a *Citrus* plant and use thereof.

BACKGROUND

*Citrus* plants are the main fruit trees grown in southern China and have important economic values. *Citrus* plants are still mainly grown outdoors, and abiotic stresses in the natural climate (such as low temperature, drought, and high salt) severely limit the growth, yield, quality, and geographical distribution of *Citrus* plants. In recent decades, researchers have conducted extensive studies to elucidate the molecular mechanisms of plant adaptation to drought and salt stresses, and have established that transcriptional and post-transcriptional gene expression regulation is an important strategy for plants to combat these two stresses. Epicuticular wax, a hydrophobic barrier covering the epicuticula on terrestrial organs of *Citrus* plants, has the important function of preventing non-stomatal water loss in *Citrus* plants and is therefore closely related to resistance of the *Citrus* plants to abiotic stresses such as drought and high salt. Therefore, it still remains an important direction of breeding work to increase the epicuticular wax content of *Citrus* plants and thereby improve the drought and salt resistance of *Citrus* plants using modern genetic engineering breeding.

Plant miRNAs are a class of non-coding RNAs (ncRNAs) of approximately 20 to 24 nucleotides. The important roles of miRNAs in post-transcriptional genetic regulation have been extensively studied and characterized in different plant species, including the regulation of plant growth and development as well as responses to biotic and abiotic stresses. The miRNA regulates target genes mainly through two mechanisms: one is to directly cleave a target mRNA; the other is to inhibit translation of the target mRNA. For example, overexpression of soybean miR172c can enhance drought and salt resistance in *Arabidopsis*; overexpression of miR393 in rice leads to increased tillering, early flowering, and reduced salt and drought resistance; and potato miR811, miR814, miR835, and miR4398 are identified as drought regulation-related miRNAs.

Currently, there are only a few reports on miRNA regulating plant epicuticular wax synthesis. For example, rice osa-miR1848 can inhibit epicuticular wax synthesis. *Arabidopsis* miRW1 negatively regulates β-diketone accumulation in wax components. The bna-miR165a-5p, screened from wax-deficient rapeseed by high-throughput sequencing, can inhibit wax accumulation in the rapeseed. However, there is no report on miRNAs regulating the synthesis of *citrus* epicuticular wax.

SUMMARY

In view of this, an objective of the present disclosure is to provide an miRNA related to resistance and a leaf epicuticular wax content of a *Citrus* plant and use thereof, where the miRNA is named csi-miRn0008. A csi-miRn0008 silencing expression vector through the short tandem target mimic (STTM) technology, and then the vector is introduced into a target plant, thus effectively regulating leaf epicuticular wax content, drought resistance, and salt resistance of a plant (especially the *Citrus* plant).

To achieve the above objective, the present disclosure provides the following technical solutions:

The present disclosure provides an miRNA related to resistance and a leaf epicuticular wax content of a *Citrus* plant, where the miRNA is named csi-miRn0008; and the csi-miRn0008 has a mature sequence set forth in SEQ ID NO: 1 and a precursor sequence set forth in SEQ ID NO: 2.

Preferably, a nucleotide sequence of a DNA molecule encoding the precursor sequence of the csi-miRn0008 is set forth in SEQ ID NO: 3.

The present disclosure further provides an expression vector, where the expression vector carries an expression cassette containing a csi-miRn0008 mimic target tandem sequence, and the csi-miRn0008 mimic target tandem sequence is set forth in SEQ ID NO: 4.

The present disclosure further provides an engineered strain containing the expression vector.

The present disclosure further provides a method for improving resistance and a leaf epicuticular wax content of a *Citrus* plant, including improving the resistance and the leaf epicuticular wax content of the *Citrus* plant by inhibiting expression of the miRNA in the *Citrus* plant.

Preferably, the resistance includes drought resistance and salt resistance.

Preferably, a synthesized csi-miRn0008 mimic target tandem sequence is ligated to a linear d35S-pBI121 vector to construct a csi-miRn0008 silencing expression vector; and the csi-miRn0008 silencing expression vector is introduced into the *Citrus* plant using an *Agrobacterium*-mediated method to cultivate a transgenic *Citrus* plant with an increased leaf epicuticular wax content and enhanced resistance.

More preferably, the linear d35S-pBI121 vector is driven by a 2×35S promoter.

More preferably, the *Agrobacterium*-mediated method employs an *Agrobacterium* strain GV3101.

The present disclosure further provides use of the miRNA, or the expression vector, or the engineered strain, or the method in improving a resistant variety of a *Citrus* plant and/or increasing a leaf epicuticular wax content of the *Citrus* plant.

Compared with the prior art, the present disclosure has the following beneficial effects:

In the present disclosure, csi-miRn0008 extracted from Newhall navel orange is used to regulate the leaf epicuticular wax content, drought resistance, and salt resistance of plants, which is beneficial to studying the response mechanism of plants to adverse stress, thereby cultivating stress-resistant plants. A DNA molecule encoding a precursor sequence of the csi-miRn0008 is used to obtain a csi-miRn0008 silencing expression vector through the STTM technology, and then the csi-miRn0008 silencing expression vector is introduced into a target plant, thus effectively regulating leaf epicuticular wax content, drought resistance, and salt resistance of a plant (especially the *Citrus* plant). The discovery of the miRNA that regulates leaf epicuticular wax synthesis, drought and salt resistance in *Citrus* plants is a major breakthrough in the field of molecular biology research on *citrus* stress resistance, and provides a new idea for improving *citrus* stress resistance. The present disclosure enrichs existing research results in the field of miRNAs, and lay a theoretical foundation and provide high-quality gene resources for breeding novel *citrus* stress-resistant varieties.

DETAILED DESCRIPTION OF THE EMBODIMENTS

Figure 1:
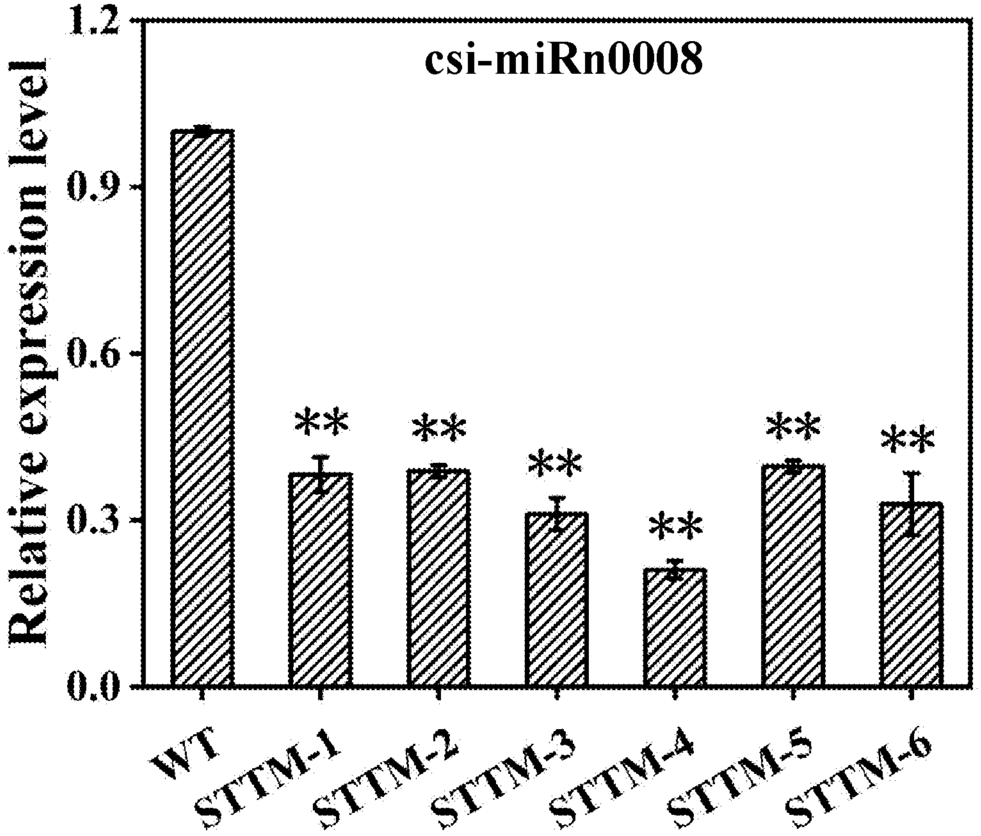
FIG. 1 shows the relative expression levels of miRn0008 in leaves of different strains of wild-type lemon and csi-miRn0008 silencing expression lemon.

The present disclosure provides an miRNA related to resistance and a leaf epicuticular wax content of a *Citrus* plant, where the miRNA is named csi-miRn0008, with a mature sequence set forth in SEQ ID NO: 1, CGGAACGGCGCGGUGUCCGCU; and the csi-miRn0008 has a precursor sequence set forth in SEQ ID NO: 2,

```
ACACAUUGGGGCCAGGACGCUGUCCUUCCACAACUUGAAUAUCAUAGUU
AUGAAUUACGCCGGCAGCCACAGCUUUCAUUUGAGUGAAAGCGACCUCU
UUGCCUAAACAAGUCCUUGGUCCUGCAUUAAAUGAGAAGAACUUGUACG
ACGGCUCCCAUUUGAUCCCUCCACUUUCAGAAAUCCAUCUUUCAGGCCU
AAAUUCCAAGCAAUCUUCUCCCCAUAUUGACUUCAUUCUCCCCAUUGCA
UACAGAGAAAACAAGAUCUUUGUUCUCGGAACGGCGCGGUGUCCGCUUG
GAAGAGUG.
```

In the present disclosure, a DNA molecule encoding the precursor sequence of the csi-miRn0008 has the nucleotide sequence set forth in SEQ ID NO: 3, as follows:

```
ACACATTGGGGCCAGGACGCTGTCCTTCCACAACTTGAATATCATAGTT
ATGAATTACGCCGGCAGCCACAGCTTTCATTTGAGTGAAAGCGACCTCT
TTGCCTAAACAAGTCCTTGGTCCTGCATTAAATGAGAAGAACTTGTACG
ACGGCTCCCATTTGATCCCTCCACTTTCAGAAATCCATCTTTCAGGCCT
AAATTCCAAGCAATCTTCTCCCCATATTGACTTCATTCTCCCCATTGCA
TACAGAGAAAACAAGATCTTTGTTCTCGGAACGGCGCGGTGTCCGCTTG
GAAGAGTG.
```

The present disclosure further provides an expression vector, where the expression vector carries an expression cassette containing a csi-miRn0008 mimic target tandem sequence, and the csi-miRn0008 mimic target tandem sequence is set forth in SEQ ID NO: 4, as follows:

```
ATTTGGAGAGAACACGGGATCCAGCGGACACCGAGTCGCCGTTCCGGTT
GTTGTTGTTATGGTCTAATTTAAATATGGTCTAAAGAAGAAGAATAGCG
GACACCGAGTCGCCGTTCCGGAGCTCGAATTTCCCCGATCGT.
```

The present disclosure further provides an engineered strain containing the expression vector.

The present disclosure further provides a method for improving resistance and a leaf epicuticular wax content of a *Citrus* plant, including improving the resistance and the leaf epicuticular wax content of the *Citrus* plant by inhibiting expression of the miRNA in the *Citrus* plant. In an embodiment of the present disclosure, a method for inhibiting expression of the miRNA (csi-miRn0008) includes: using STTM technology that can specifically inhibit a certain miRNA, that is, artificially synthesizing a sequence that can complementarily pair with a specific miRNA mature sequence but cannot cause the miRNA to cut a target gene, and transcribing the sequence under the drive of a 2×35S promoter (d35S), where a resulting transcription product can effectively inhibit silencing expression of abundance of the miRNA.

In the present disclosure, the resistance includes drought resistance and salt resistance. The drought resistance is drought tolerance, which refers to the ability of plants to adapt to and resist drought; the salt resistance is salt tolerance, which refers to the ability of plants to tolerate salt damages.

In the present disclosure, a synthesized csi-miRn0008 mimic target tandem sequence is ligated to a linear d35S-pBI121 vector to construct a csi-miRn0008 silencing expression vector; and the csi-miRn0008 silencing expression vector is introduced into the *Citrus* plant using an *Agrobacterium*-mediated method to cultivate a transgenic *Citrus* plant with an increased leaf epicuticular wax content and enhanced resistance.

In the present disclosure, the linear d35S-pBI121 vector is driven by a 2×35S promoter.

In the present disclosure, the *Agrobacterium*-mediated method employs an *Agrobacterium* strain GV3101.

The present disclosure further provides use of the miRNA, or the expression vector, or the engineered strain, or the method in improving a resistant variety of a *Citrus* plant and/or increasing a leaf epicuticular wax content of the *Citrus* plant. In the present disclosure, the *Citrus* plant includes but is not limited to sweet orange, pomelo, tangerine, mandarin orange, citron, lemon, and kumquat.

To facilitate a better understanding of the present disclosure, the present disclosure is described in detail below with reference to the drawings and specific embodiments. In the following examples, unless otherwise specified, the experimental methods used are conventional, and the materials and reagents used are commercially available.

Example 1 Extraction of DNA Molecule Encoding Precursor Sequence of csi-miRn0008

(1) Extraction of Plant Genomic DNA

A leaf DNA of Newhall navel orange was extracted using a plant genomic DNA extraction kit (TIANGEN Biotech (Beijing) Co., Ltd.), and the detailed steps were shown in its instruction manual.

(2) PCR Amplification

The genomic DNA extracted in step (1) was used as a template for PCR according to the following system:

TABLE 1

PCR amplification system (50 μL)

| Reaction mixture | Volume |
|---|---|
| DNA | 1 μL |
| 2 × SuperStar HiFi Plus PCR Mix(Dye) | 25 μL |
| Primer F | 2 μL |
| Primer R | 2 μL |
| $ddH_2O$ | 20 μL |
| Total | 50 μL |

```
Upstream primer Primer F:
                                  (SEQ ID NO: 5)
5'-ACACATTGGGGCCAGGAC-3'

Downstream primer Primer R:
                                  (SEQ ID NO: 6)
5'-CACTCTTCCAAGCGGACA-3'.
```

The PCR amplification procedure was described in the instruction manual of the ultra-fidelity PCR mix (Beijing GenStar Biotech Co., Ltd.).

The amplified target fragment was separated by 1.5% agarose gel electrophoresis to obtain a band with a molecular weight of approximately 302 bp. The gel block containing the target gene was cut with a clean blade on a UV projection gel cutting table and then placed in a 2 mL centrifuge tube. The product was recovered using an agarose gel DNA recovery kit (TIANGEN Biotech (Beijing) Co., Ltd.).

(3) Ligation and Transformation of Target Fragment and Sequencing Vector

The target fragment was ligated to the sequencing vector using the pClone007 Blunt Vector Kit (Beijing Tsingke Biotech Co., Ltd.), and the ligation product was transformed into *Escherichia coli* Trans5a competent cells (Beijing TransGen Biotech Co., Ltd.). Detailed steps were described in the instruction manual. Single clones were selected for colony PCR detection, where the PCR primers, system, and procedure were the same as those in step (2). The selected positive colonies were sent to Sangon Biotech (Shanghai) Co., Ltd. for sequencing.

Example 2 Construction of csi-miRn0008 Silencing Expression Vector

The STTM technology that can specifically inhibit a certain miRNA was adopted for csi-miRn0008 silencing expression, including: a sequence that can complementarily pair with a specific miRNA mature sequence but cannot cause the miRNA to cut a target gene was artificially synthesized, and the sequence was transcribed under the drive of a 2×35S promoter (d35S), where a resulting transcription product can effectively inhibit abundance of the miRNA.

(1) Design of STTM0008 Sequence

Two mature sequences of csi-miRn0008 were reversely complemented, and three bases "AGT" were added between the 11th and 12th bases at the cleavage site of csi-miRn0008. The two fragments were ligated with a 48 bp sequence that could form a hairpin structure by itself, and then 22 bp of sequences located upstream and downstream of the BamH I and Sac I restriction sites on a pBI121 vector were added to 5' and 3' ends of the entire sequence, respectively, to allow subsequent homologous recombination reactions. The finally designed sequences were as follows:

(SEQ ID NO: 4)

ATTTGGAGAGAACACGGGATCC*AGCGGACACCG*AGT*CGCCGTTCCG*gtt gttgttgttatggtctaatttaaatatggtctaaagaagaagaat*AGCG*

*GACACCG*AGT*CGCCGTTCCG*GAGCTCGAATTTCCCCGATCGT.

The underlined part represented a homologous recombination sequence on the pBI121 vector, the italic part represented a reverse complementary sequence of the csi-miRn0008 mature sequence, the bold part represented an introduced bridge sequence, and the lowercase part represented an intermediate 48 bp ligation sequence. The designed sequences were sent to Sangon Biotech (Shanghai) Co., Ltd. for synthesis.

(2) Construction of d35S-pBI121 Vector

Amplification primers were designed based on a sequence of 35S on the pBI121 vector, and Xba I and BamH I restriction sites and protective bases were added to the 5' end of the designed primers, where the primer sequences were as follows:

```
upstream primer F-35S:
                                        (SEQ ID NO: 7)
5'-ATGCTCTAGAAGATTAGCCTTTTCAATTTCAG-3';
and

downstream primer R-35S:
                                        (SEQ ID NO: 8)
5'-CGCGGATCCCGTGTTCTCTCCAAATGAAATG-3'.
```

The 35S sequence was amplified using the pBI121 vector plasmid as a template with an ultra-fidelity PCR mix system. The amplified products were separated by 1% agarose gel electrophoresis, recovered from the gel, ligated to a sequencing vector, and then transformed into *Escherichia coli* Trans5a competent cells. Single clones were selected for PCR, and the positive colonies were selected and sent to a biological company for sequencing (the method referred to Example 1).

A plasmid of the positive colonies was extracted using a plasmid extraction kit (TIANGEN Biotech (Beijing) Co., Ltd.), and the plasmid and pBI121 empty vector was double-digested with Xba I and BamH I, respectively. The enzyme digestion system was as follows:

TABLE 2

| Reaction system of double enzyme digestion (50 μL) | |
|---|---|
| Reaction mixture | Volume |
| Plasmid DNA | 25 μL |
| 10 × FuniCut ™ Buffer | 5 μL |
| Xba I | 2.5 μL |
| BamH I | 2.5 μL |
| $ddH_2O$ | 15 μL |
| Total | 50 μL |

A procedure of enzyme digestion was described in the instruction manual of a rapid restriction endonuclease used (Yeasen Biotechnology (Shanghai) Co., Ltd.). The products after double digestion were separated by 1% agarose gel electrophoresis, and the 35S fragment and the linear pBI121 vector were recovered. The two recovered fragments were subjected to ligation reaction according to the system in Table 3:

TABLE 3

| Ligation reaction system (10 μL) | |
|---|---|
| Reaction mixture | Volume |
| 10 × Buffer | 1.0 μL |
| T4 ligase (350 U/μL) | 0.5 μL |
| 35S fragment | 2.0 μL |
| pBI121 vector large fragment | 4.0 μL |
| $ddH_2O$ | Supplementing to 10.0 μL |

The ligation was conducted at 16° C. for 16 h.

The ligation product was transformed into *E. coli* Trans5a competent cells, and a single clone was selected. A pair of primers were designed before and after the desired constructed d35S:

```
upstream primer F-d35S:
                                    (SEQ ID NO: 9)
5'-TATGCTTCCGGCTCGTATG-3';
and

downstream primer R-d35S:
                                   (SEQ ID NO: 10)
5'-ATCCAGACTGAATGCCCAC-3'.
```

The above primers were used for PCR, and positive colonies were selected and sent to a biological company for sequencing (the method referred to Example 1). The positive clone bacterial solution verified by sequencing was revived and a plasmid was extracted.

(3) Construction of csi-miRn0008 Silencing Expression Vector

The STTM0008 sequence synthesized by the company was on the pUC19 vector, and transformed into *Escherichia coli*. A single colony was selected to allow PCR using universal primers M13 (upstream primer M13-F: TGTAAAACGACGGCCAGT (SEQ ID NO: 11); downstream primer M13-R: CAGGAAACAGCTATGACC (SEQ ID NO: 12)) to obtain a positive bacterial solution. A pair of amplification primers was designed based on the designed STTM0008 sequence:

```
upstream primer F-STTM:
                                   (SEQ ID NO: 13)
5'-ATTTGGAGAGAACACGGGATC-3';
and

downstream primer R-STTM:
                                   (SEQ ID NO: 14)
5'-CGATCGGGGAAATTCGAG-3'.
```

The STTM0008 sequence was amplified using the above positive bacterial solution as a template with an ultra-fidelity PCR mix system. The amplified products were separated by 1% agarose gel electrophoresis, recovered from the gel, and stored for later use. The d35S-pBI121 vector obtained in step (2) was double-digested with Sac I and BamH I, and the products after double digestion were separated by 1% agarose gel electrophoresis, and the linear d35S-pBI121 vector was recovered. The recovered STTM0008 sequence was ligated with the linear d35S-pBI121 vector, and a ligation product was transformed into *Escherichia coli*, and PCR was conducted using the above primers. The positive colonies were selected and sent to a biological company for sequencing, and a positive plasmid with correct sequencing was named STTM0008.

(4) *Agrobacterium* Transformation of STTM0008

The constructed vector STTM0008 was transformed into *Agrobacterium* strain GV3101 (Shanghai Weidi Biotech Co., Ltd.). Detailed steps were shown in the instruction manual. A single colony was selected to allow PCR with the primers in step (3), 20% glycerol was added to the positive bacterial solution and mixed well, and a resulting bacterial solution was the *Agrobacterium* strain containing the STTM0008 vector plasmid, which was stored at −80° C. for future use.

Example 3 Preparation of Transgenic Lemon with csi-miRn0008 Silencing Expression (1) Sowing The seeds from lemon fruit were taken out, washed with double distilled water and air-dried, the outer seed coat of the dried seeds was peeled off, and a cross was made on the seeds with a blade. The treated seeds were immersed in double-distilled water for more than 1 h, sown in a substrate (soil:vermiculite=3:1), watered thoroughly, and grown in a culture room (25° C., 16 h light/8 h dark, 80% relative humidity) for 4 weeks.

(2) Preparation of *Agrobacterium* Infection Solution

*Agrobacterium* containing the STTM0008 vector plasmid stored at −80° C. was transferred into a YEB Liquid Medium (Beijing Solarbio Co., Ltd.) containing 50 mg/L kanamycin and 20 mg/L rifampicin, and cultured at 28° C., 200 r/min until the bacterial solution was at about $OD_{600}$=1.0, then expanded to about $OD_{600}$=0.7, and a supernatant was removed after centrifugation. The bacterial cells were resuspended in MS broth (Qingdao Hi-Tech Industrial Park Hope Bio-Technology Co., Ltd.) containing 100 μmol/L acetosyringone, and then cultured at 28° C., 200 r/min for 30 min before use for infection.

(3) In-Situ Transformation 4-week-old seedlings of lemon seeds were cut at a true leaf attachment site with a blade, and a 10 μL pipette tip imbibed with an infection solution was placed upside down on a resulting incision such that the incision was immersed in the infection solution. 45 min after infection, a sterile 10 μL pipette tip was placed upside down on the incision to keep it moist, and then covered with a black plastic film for co-cultivation. To improve a transformation efficiency, after 3 d of co-cultivation, the black film was removed and the pipette tip was removed for secondary infection. After 3 d, the black film was peeled off again, the pipette tip was removed, and the incision was gently wiped 2 to 3 times with 50 mg/L kanamycin solution to make it covered with obvious antibiotic solution. The incision was inverted with a pipette tip and dark-treated to promote the regeneration of the incision. After 2 weeks, the black film was removed and the seedlings lemon seeds continued to grow under the conditions of the culture room.

(4) Identification of Positive Lemon Transformed Plants

The lemon leaves were placed in a 2 mL centrifuge tube, an appropriate amount of liquid nitrogen was added, and the leaves were ground with a 1 mL pipette tip having a burned-flat end pre-cooled with liquid nitrogen, and the leaf DNA was extracted using a Cetyltrimethylammonium Bromide (CTAB) method, as follows:

i) 650 μL of a mixture of 2×CTAB extraction buffer and β-mercaptoethanol (Beijing Solarbio Co., Ltd.) (volume ratio 99:1) was added into a 2 mL centrifuge tube containing the sample, shaken to mix well, and placed in a 65° C. water bath for 60 min;
ii) 650 μL of a mixture of chloroform and isoamyl alcohol (Sichuan Xilong Scientific Co., Ltd.) (volume ratio 24:1) was added, extracted for 2 min to 3 min, mixed well, and centrifuged at 12,000 rpm for 5 min;
iii) about 600 μL of the supernatant was pipetted into a new 1.5 mL centrifuge tube, added with an equal volume of isopropanol (Sichuan Xilong Scientific Co., Ltd.), mixed well by inversion, allowed to stand for 10 min, and centrifuged at 12,000 rpm for 2 min;
iv) a supernatant was removed, 900 μL of 75% ethanol was added, mixed well by inversion, centrifuged at 12,000 rpm for 1 min, and a supernatant was removed;
v) a resulting precipitate was treated with a rotary evaporator under V-AL conditions for 10 min;
vi) 50 μL of $ddH_2O$ was added into the centrifuge tube and placed in a 4° C. refrigerator overnight.

Primers were designed based on the 35S sequence on the STTM0008 vector:

```
upstream primer 35S-F:
                                    (SEQ ID NO: 15)
5'-TAACAGAACTCGCCGTAAAGAC-3';
and

downstream primer R-STTM:
                                    (SEQ ID NO: 14)
5'-CGATCGGGGAAATTCGAG-3'.
```

The extracted DNA was used as a template for PCR amplification to identify the positive lemon transformed plants, where a PCR system was halved and the procedures were the same as step (2) of Example 1.

(5) Identification of csi-miRn0008 Expression in Leaves of Positive Transgenic Lemon Lines Real-time fluorescence quantitative PCR (qPCR) was conducted to detect the expression level of csi-miRn0008 in the leaves of wild-type lemon and positive transgenic lemon lines. Total RNA was extracted from wild-type and transgenic lemon leaves using a total RNA extraction kit (Promega (Beijing) Biotech Co., Ltd.), and detailed steps were described in the instruction manual. According to the instructions of the miRNA First-Strand cDNA Synthesis (Stem-Loop Method) Kit (Sangon Biotech (Shanghai) Co., Ltd.) and the mature sequence of csi-miRn0008, miRNA stem-loop primers were designed and cDNA was synthesized.

Primer Sequences:

```
                                    (SEQ ID NO: 16)
5'-GTCGTATCCAGTGCAGGGTCCGAGGTATTCGCACTGGATACGACAG

CGGA-3'.
```

Then, qPCR was conducted using the miRNA Fluorescence Quantitative PCR Kit (Dye Method) (Sangon Biotech (Shanghai) Co., Ltd.), where the system and procedure were referred to the instruction manual, and the qPCR primer sequences were as follows:

```
upstream primer miRn0008-F:
                                    (SEQ ID NO: 17)
5'-GCGGAACGGCGCGGTG-3';
and

downstream primer miRn0008-R:
                                    (SEQ ID NO: 18)
5'-AGTGCAGGGTCCGAGGTATT-3'.
```

A U6 gene was used as an internal reference, and U6 primer sequences were as follows:

```
an upstream primer U6-F:
                                    (SEQ ID NO: 19)
5'-TTGGGACGATACACAGAAAATTAG-3';
and

downstream primer U6-R:
                                    (SEQ ID NO: 20)
5'-GATTTGTGCGTGTCATTCCTGTC-3'.
```

The qPCR results in FIG. 1 and Table 4 showed that the expression level of csi-miRn0008 in the leaves of transgenic lemon lines was significantly lower than that of wild-type lemons.

TABLE 4

Relative expression levels of miRn0008 in leaves of wild-type lemon and transgenic lemon of different strains

| Genotype | Relative expression level |
|---|---|
| WT | 1.00 ± 0.01 |
| STTM-1 | 0.38 ± 0.03** |
| STTM-2 | 0.39 ± 0.01** |
| STTM-3 | 0.31 ± 0.03** |
| STTM-4 | 0.21 ± 0.02** |
| STTM-5 | 0.40 ± 0.01** |
| STTM-6 | 0.33 ± 0.06** |

**indicated that the relative expression level in the leaves of transgenic lemon lines was significantly lower than that of wild-type lemon ($P < 0.01$).

Example 4 The csi-miRn0008 Silencing Expression in Increasing Leaf Epicuticular Wax Content of Transgenic Lemon (1) Detection of Leaf Water Loss and Chlorophyll Permeability The wild-type (WT) and two transgenic lemon lines (STTM-1 and STTM-2) were placed in the dark for 12 h, and their leaves were cut and weighed immediately. The leaves were placed in the dark and weighed every 1 h at room temperature (0 h to 8 h). The water loss was a ratio of the reduced mass of the leaves at a certain time point to the initial fresh weight of the leaves. Each treatment was set up with 3 to 5 replicates, and the experiment was repeated 3 times.

The wild-type and two transgenic lemon strains were placed in the dark for 12 h, their leaves were cut and immediately immersed in 50 mL of 80% ethanol solution (v/v) in a glass tube, and a resulting leachate was taken separately at 2, 4, 6, 8, 10, 12 and 24 h for absorbance determination. The entire operation was done under weak light, and absorbance of the leachate at 647 nm and 664 nm was determined using a UV spectrophotometer. The total chlorophyll micromolar amount (M) in the leachate was (M)=7.93 (A664)+19.53 (A647). The chlorophyll leaching rate at each time point was calculated based on the chlorophyll leaching amount in 24 h.

(2) Extraction and Analysis of Leaf Epicuticular Wax Components (by GC-FID)

GC-FID was conducted to determine the composition and content of wax on the leaf surface of transformed plants. Leaves of the wild-type and transgenic lemon lines with the same area and seedling age were placed in a 20 mL gas chromatography glass sample bottle. During extraction, two times of 10 mL of chromatographic-pure n-hexane were added, shaken for 30 s, and then the n-hexane solutions were combined into a new 20 mL sample bottle. The samples could be processed immediately or stored in a 4° C. refrigerator for a long time. 100 μL of 50 μg/mL n-tetracosane as an internal standard was added into the sample using a precision pipette tip and shaken to mix well. After drying the solvent n-hexane with nitrogen at 50° C. in a nitrogen blower, 50 μL of a derivatization reagent BSTFA was added, shaken to mix well, and derivatized at 100° C. for 15 min to 30 min. After the derivatization bottle cooled to room temperature, an appropriate volume of n-hexane was added and shaken to dissolve the sample. Finally, the sample was transferred to a GC loading bottle for sample analysis.

Agilent 8890 gas chromatograph was used, and a chromatographic column used was DB-5. A method for measuring leaf wax included: carrier gas: helium, flow rate: 1 mL/min, using constant flow mode. Detector: flame ionization detector (FID), 300° C.; Air:$H_2$:He=400:30:25. Inlet temperature: 300° C., splitless mode, injection volume: 1 μL. The column temperature program was as follows: initial temperature 80° C., held for 2 min, then increased to 200° C. at 40° C./min, held for 2 min, then increased to 270° C. at 10° C./min, held for 2 min, and then increased to 320° C. at 2° C./min, held for 10 min. Each peak was quantified by combining with the internal standard, and each peak was qualitatively analyzed by combining with a standard.

Figure 2A:
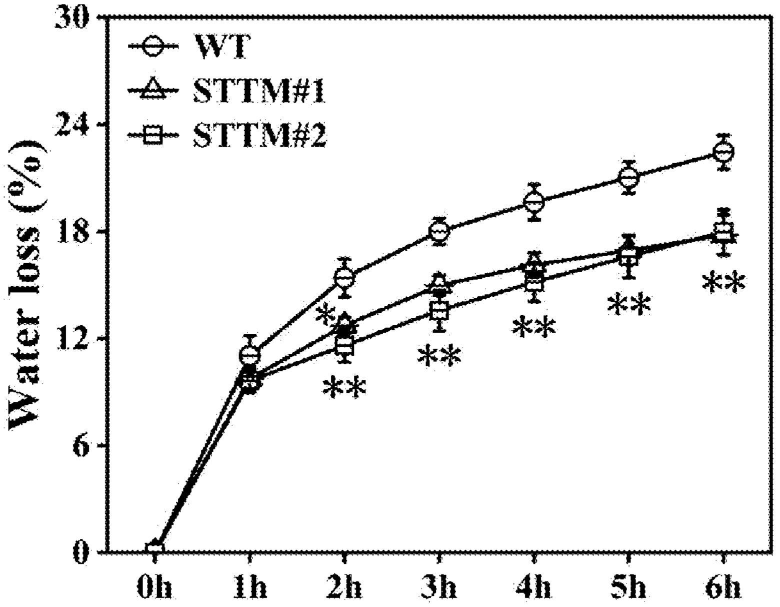
FIGS. 2A-D show the test results of water loss, chlorophyll leaching, and wax content of detached leaves of wild-type lemon and two csi-miRn0008 silencing expression lemon lines (STTM-1 and STTM-2)
Figure 2B:
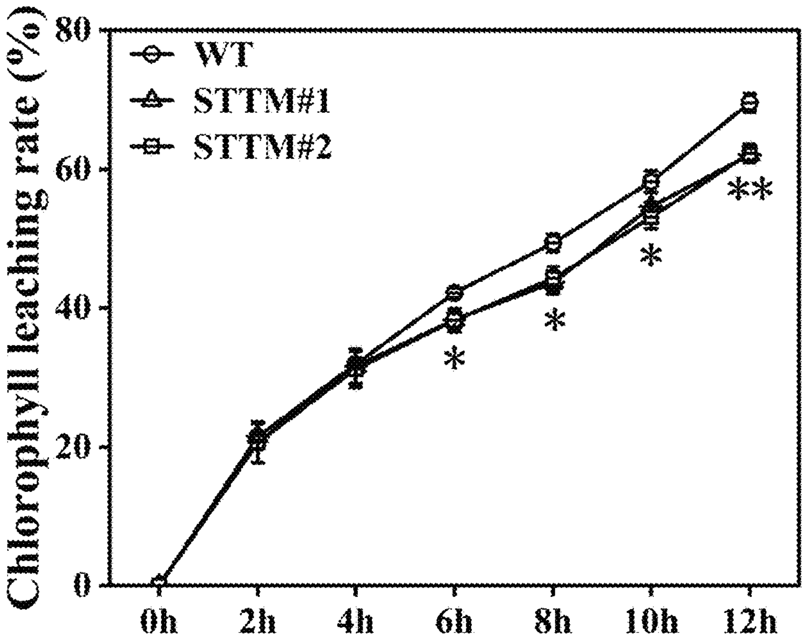

Experimental Results Showed that:

The water loss and chlorophyll leaching rate of detached leaves of the csi-miRn0008 silencing expression lemon lines (STTM-1 and STTM-2) were significantly lower than those of the wild-type lemon (WT) (FIG. 2A to FIG. 2B).

Figure 2C:
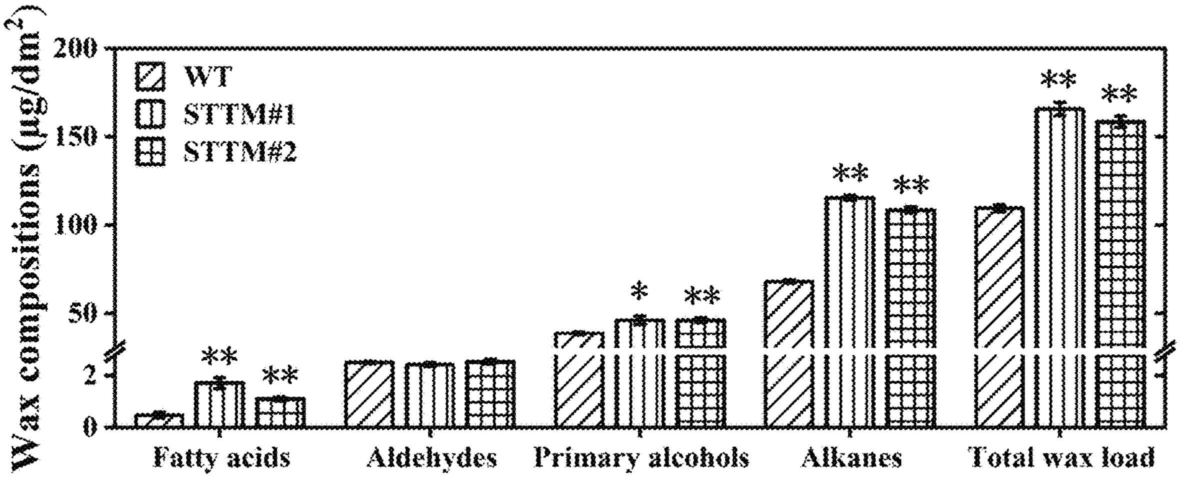
Figure 2D:
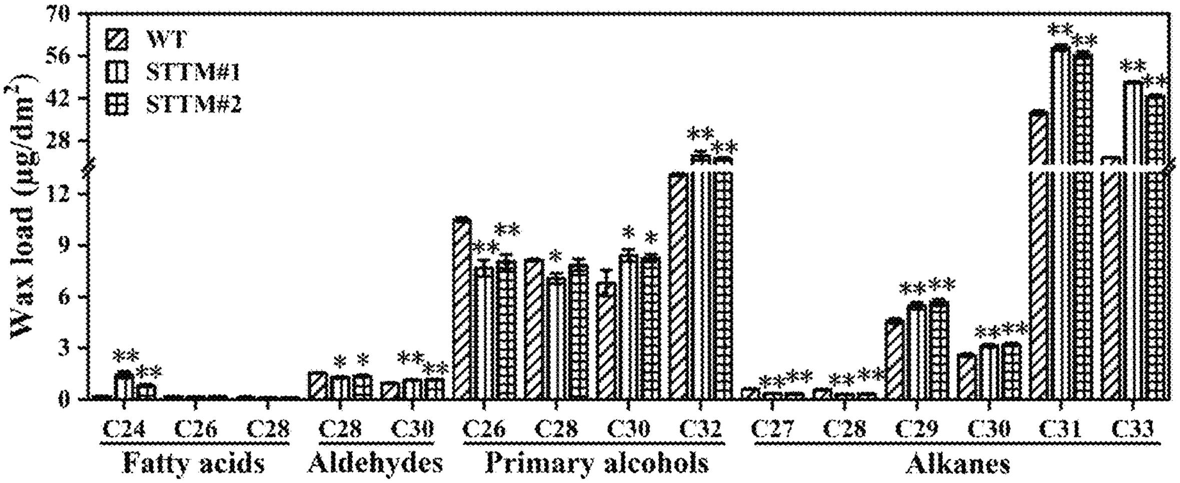

GC-MS wax content analysis showed that the total wax content of the leaves of csi-miRn0008 silencing expression lemon lines (STTM-1 and STTM-2) was significantly higher than that of the wild-type lemon. The main components of lemon leaf epicuticular wax included four types, such as fatty acids, aldehydes, primary alcohols and alkanes, where contents of 3 types, fatty acids, primary alcohols, and alkanes in the csi-miRn0008 silencing expression lemon leaves were significantly higher than those in the wild-type lemon (FIG. 2C). The contents of wax components such as C24 fatty acids, C30 aldehydes, C30-C32 primary alcohols, and C29-C33 alkanes in the leaves of transgenic lemon were significantly higher than those in wild-type lemon (FIG. 2D). * represented the significance level ($p<0.05$); ** represented the extremely significant level ($p<0.01$).

The results showed that the csi-miRn0008 silencing expression could significantly increase the total wax content and the contents of fatty acids, primary alcohols, and alkanes in the lemon leaf epicuticula.

Example 5 The Csi-miRn0008 Silencing Expression in Enhancing Drought and Salt Resistance in Transgenic Lemon (1) Drought and High-Salt Stress Treatment Wild-type lemon (WT) and 4 transgenic lemon lines (STTM-3 to STTM-6) with consistent growth were selected and subjected to drought (STTM-3 and STTM-4) and high-salt (STTM-5 and STTM-6) treatments, respectively.

Drought soil culture treatment: wild-type lemon and two transgenic lemon lines (STTM-3 and STTM-4) treated with natural drought (no watering) were photographed and tested for resistance physiological indicators 14 d later.

High-salt soil culture treatment: the wild-type and transgenic lemons were irrigated with 300 mmol/L NaCl at the same time, 100 mL per tree each time, once every 3 days, for a total of 14 days, and phenotype was photographed and resistance physiological index testing were tested.

(2) Determination of Activities of Malondialdehyde (MDA), Hydrogen Peroxide ($H_2O_2$) and Superoxide Dismutase (SOD), Peroxidase (POD), and Catalase (CAT) in Leaves.

The activities of MDA, $H_2O_2$, SOD, POD and CAT in the leaves of the two genotypes of lemon before and after drought and high-salt treatment were detected using the MDA (A003), $H_2O_2$ (A064), SOD (A001), POD (A084), and CAT (A007) detection kits produced by Nanjing Jiancheng Bioengineering Institute, and the detailed steps were shown in the instructions.

Figure 3A:
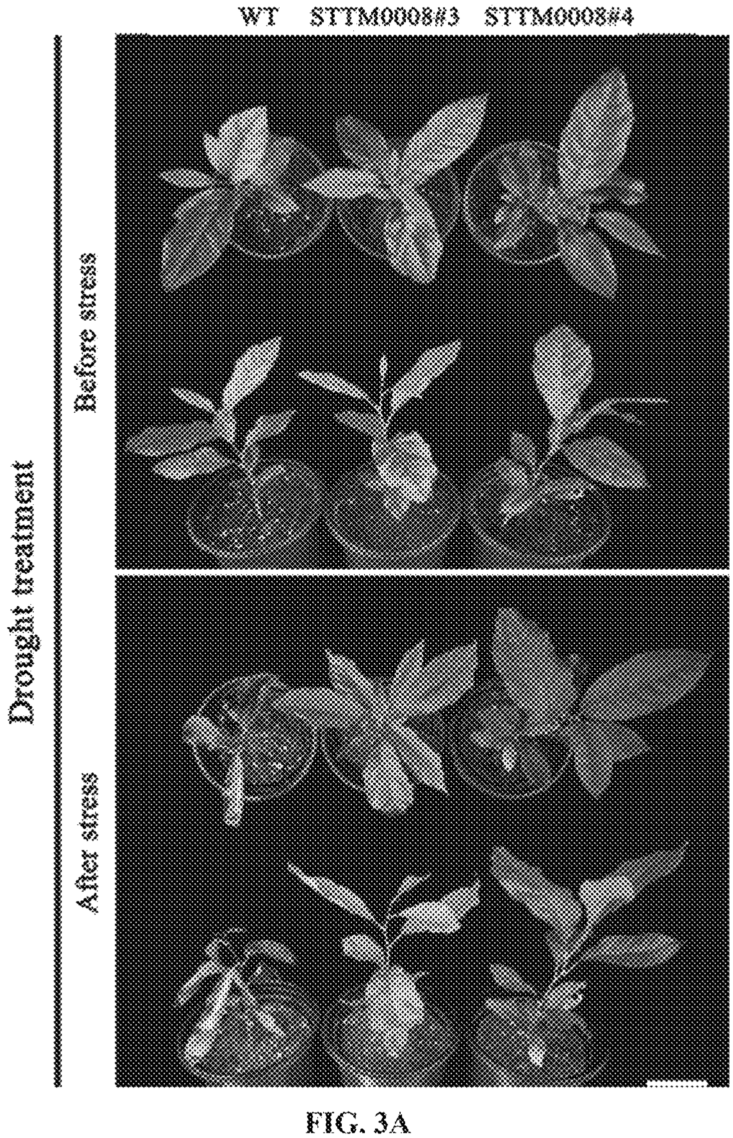
FIGS. 3A-H show the test results of phenotype and resistance physiological indexes of wild-type lemon and two csi-miRn0008 silencing expression lemon lines (STTM-3 and STTM-4) before and after drought stress.
Figure 4A:
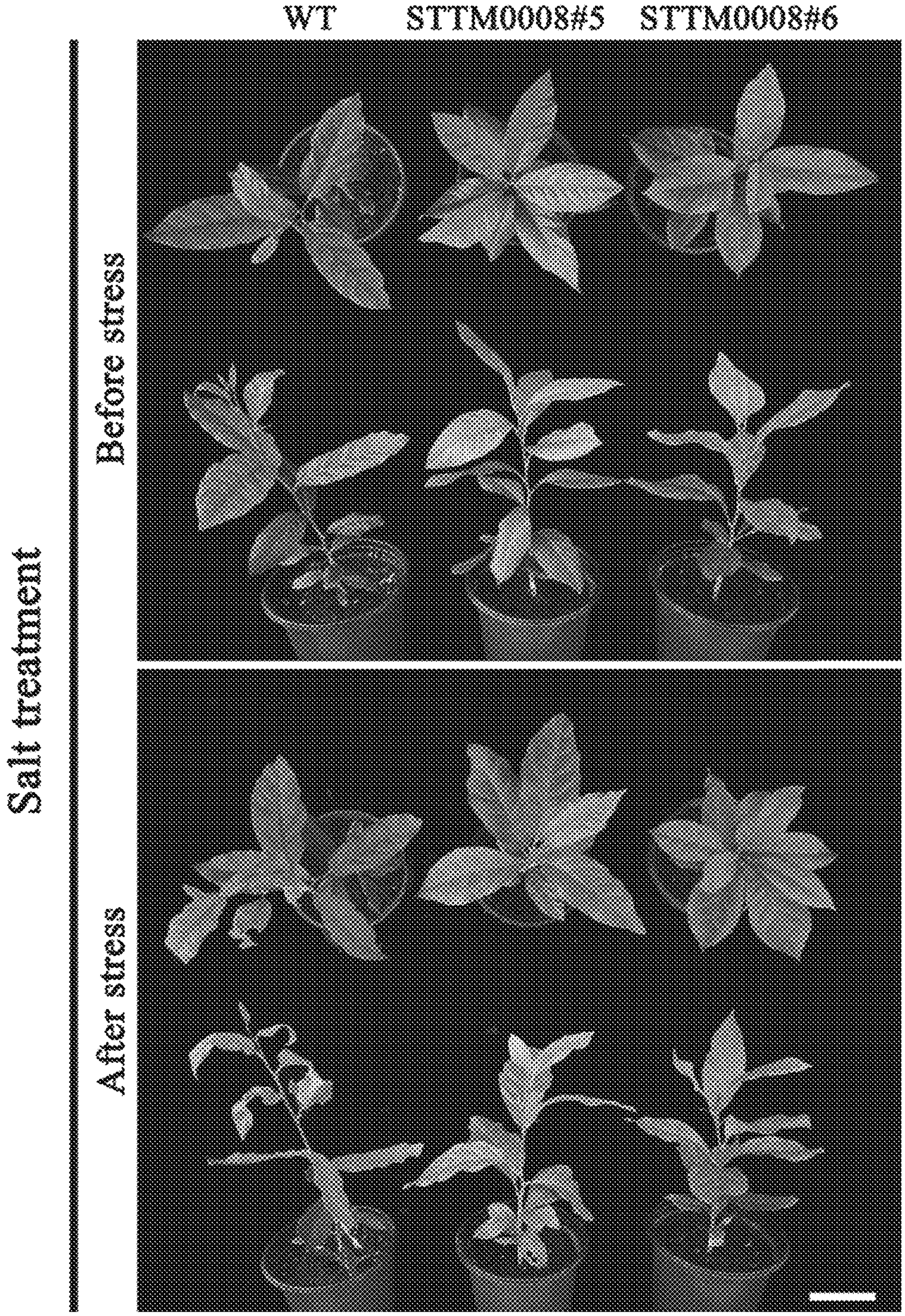
FIGS. 4A-H show the test results of phenotype and resistance physiological indexes of wild-type lemon and two csi-miRn0008 silencing expression lemon lines (STTM-5 and STTM-6) before and after high-salt stress.

Experimental Results Showed that:

Before drought and high-salt stress treatments, there was no significant phenotype difference between wild-type lemon (WT) and csi-miRn0008 silencing expression lemon lines (STTM-3 to STTM-6); after drought and high-salt stress treatments, the wild-type lemon (WT) showed severe leaf curling and drooping, while the leaf damage degree of csi-miRn0008 silencing expression lemon lines was less than that of the wild-type (FIG. 3A, FIG. 4A).

Figure 3B:
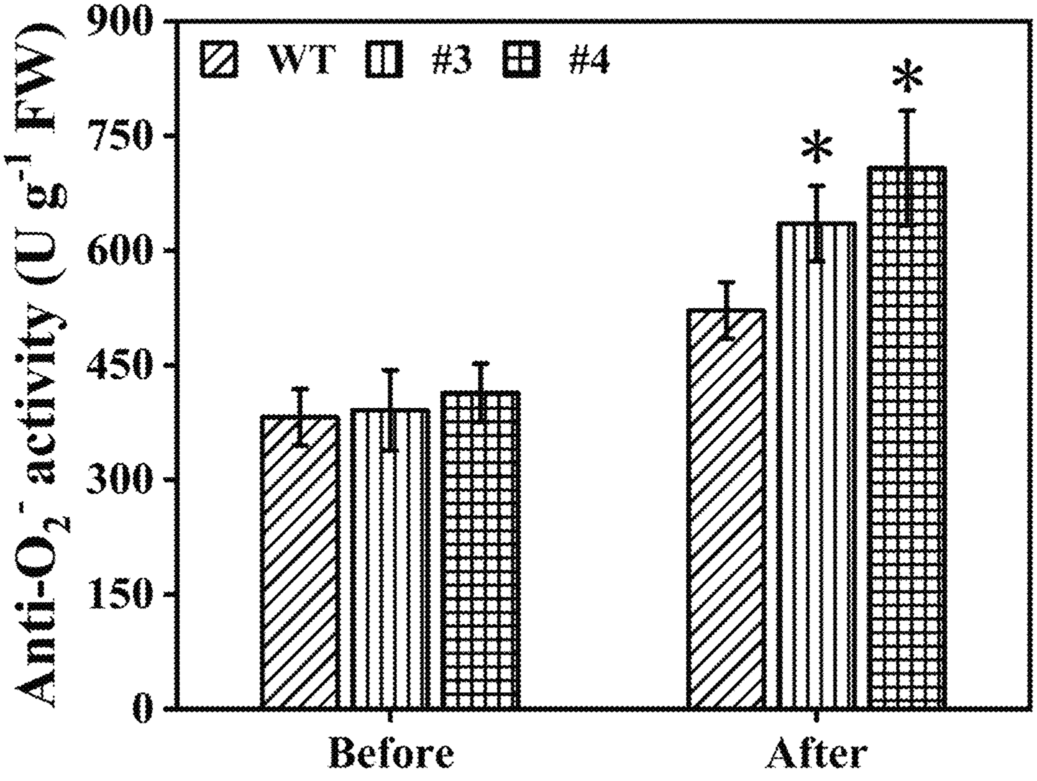
Figure 3C:
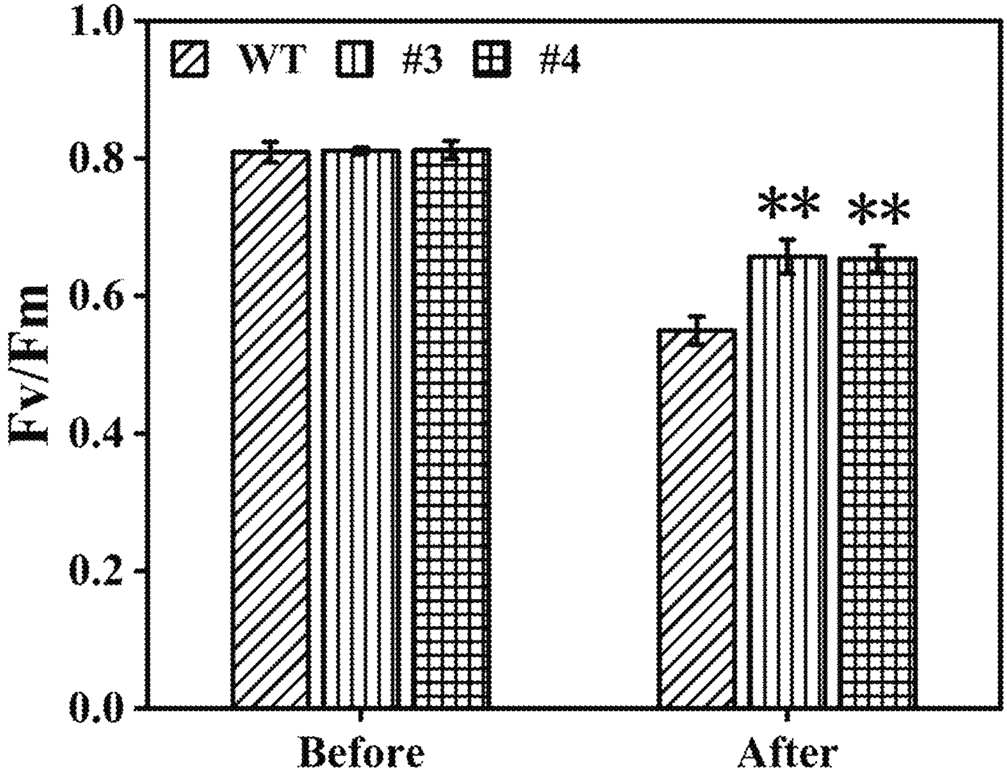
Figure 3D:
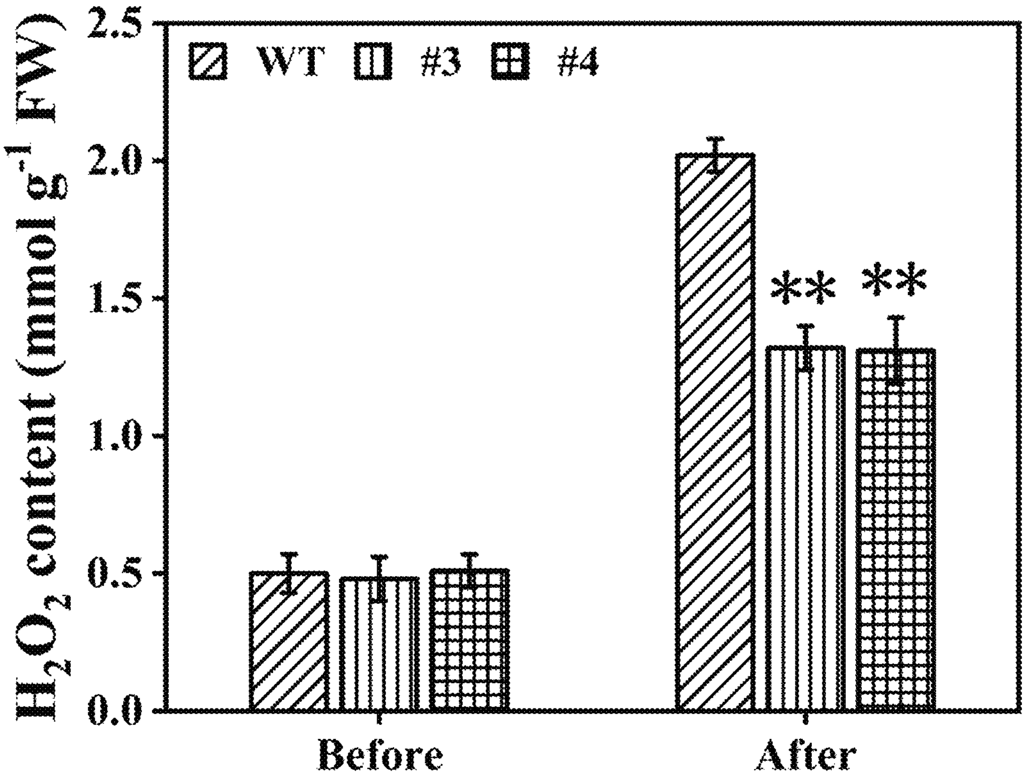
Figure 3E:
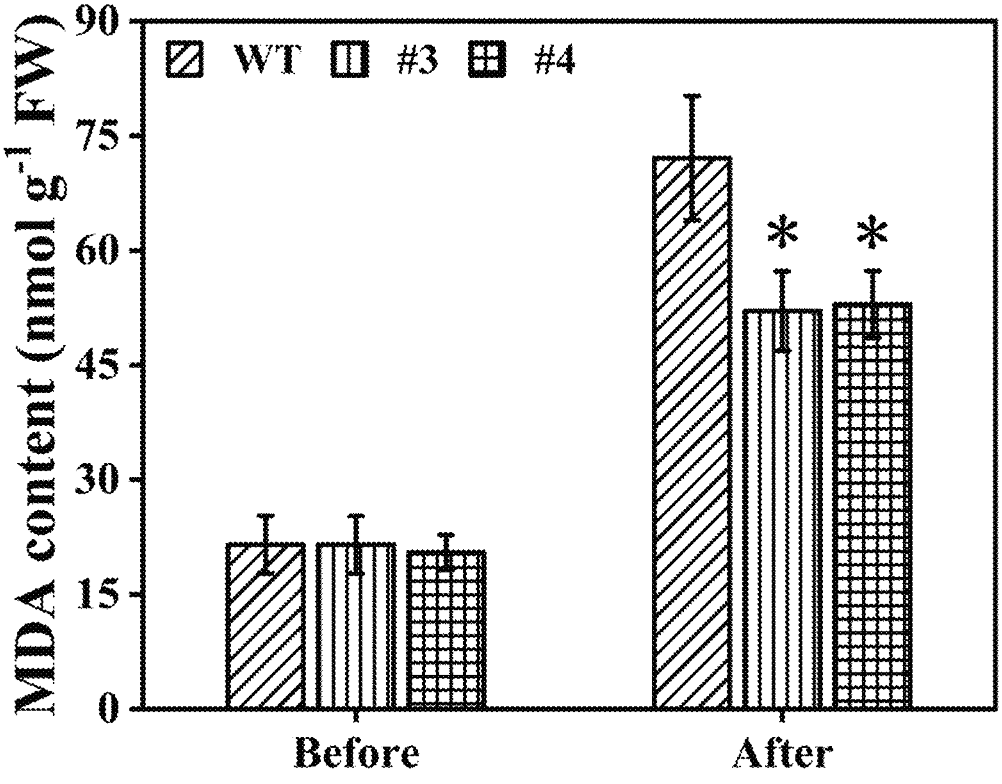
Figure 3F:
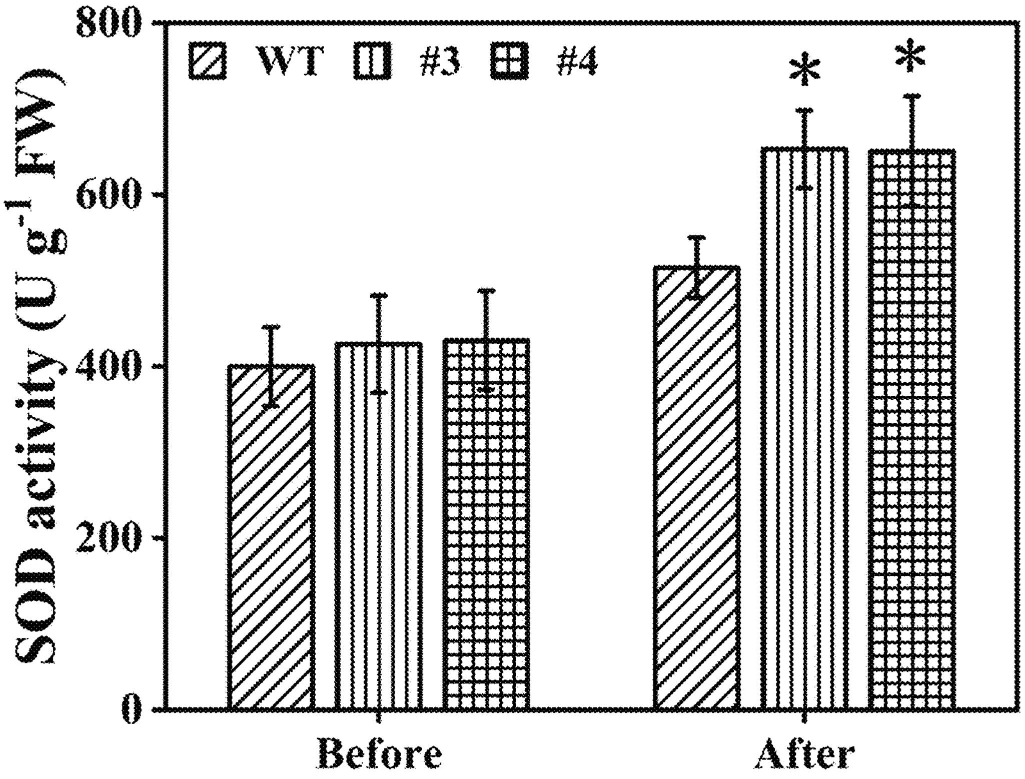
Figure 3G:
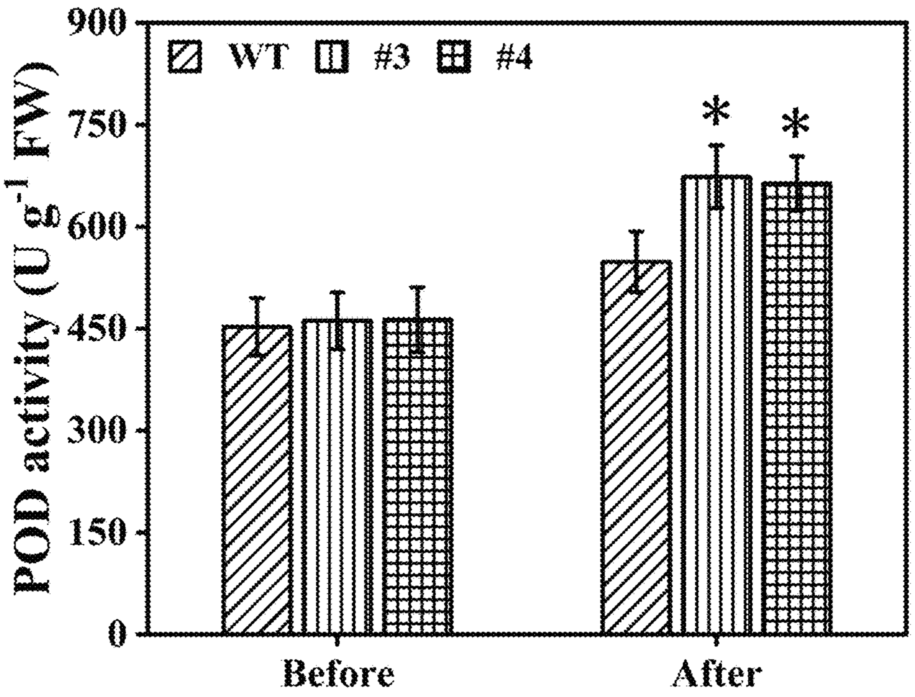
Figure 3H:
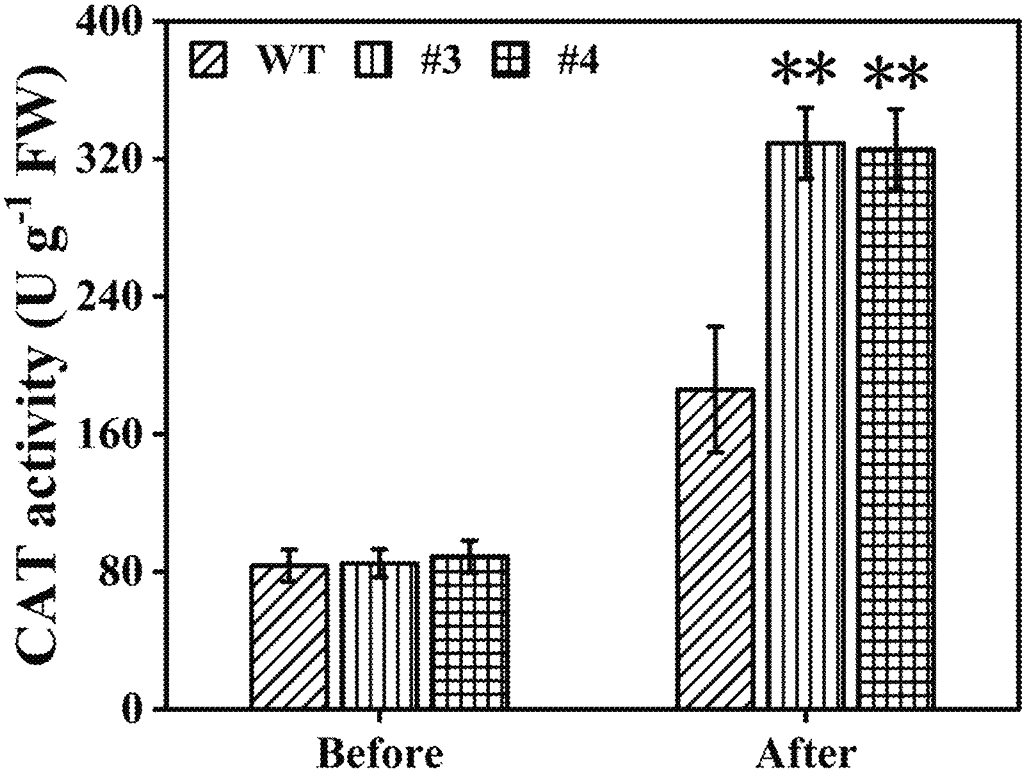
Figure 4B:
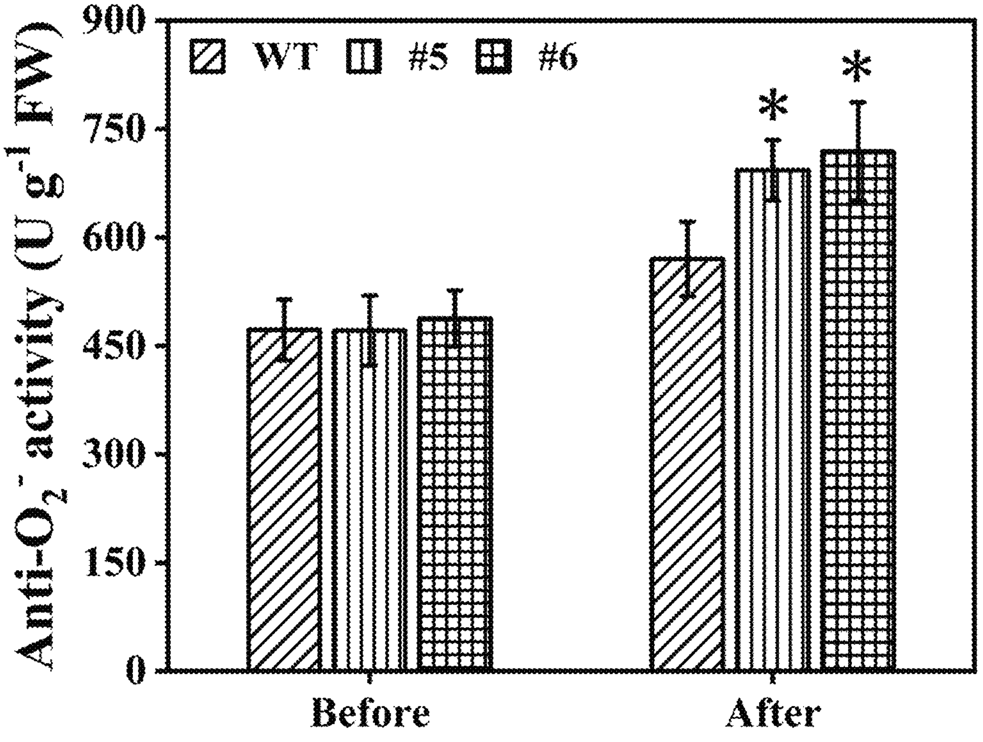
Figure 4C:
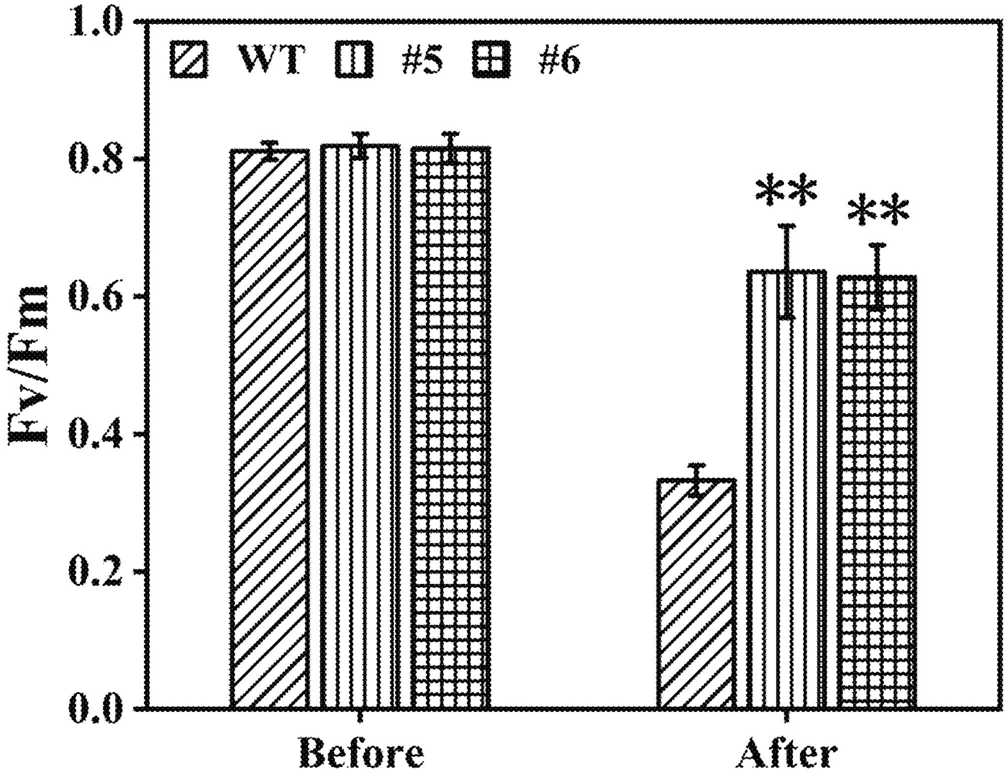
Figure 4D:
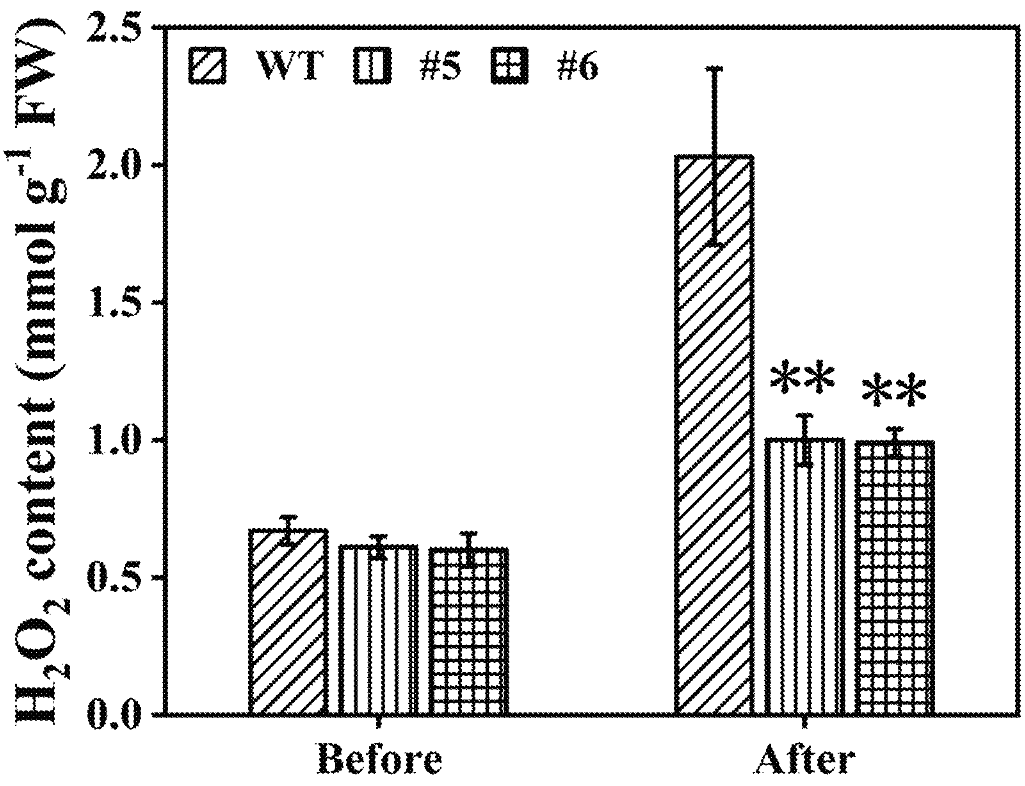
Figure 4E:
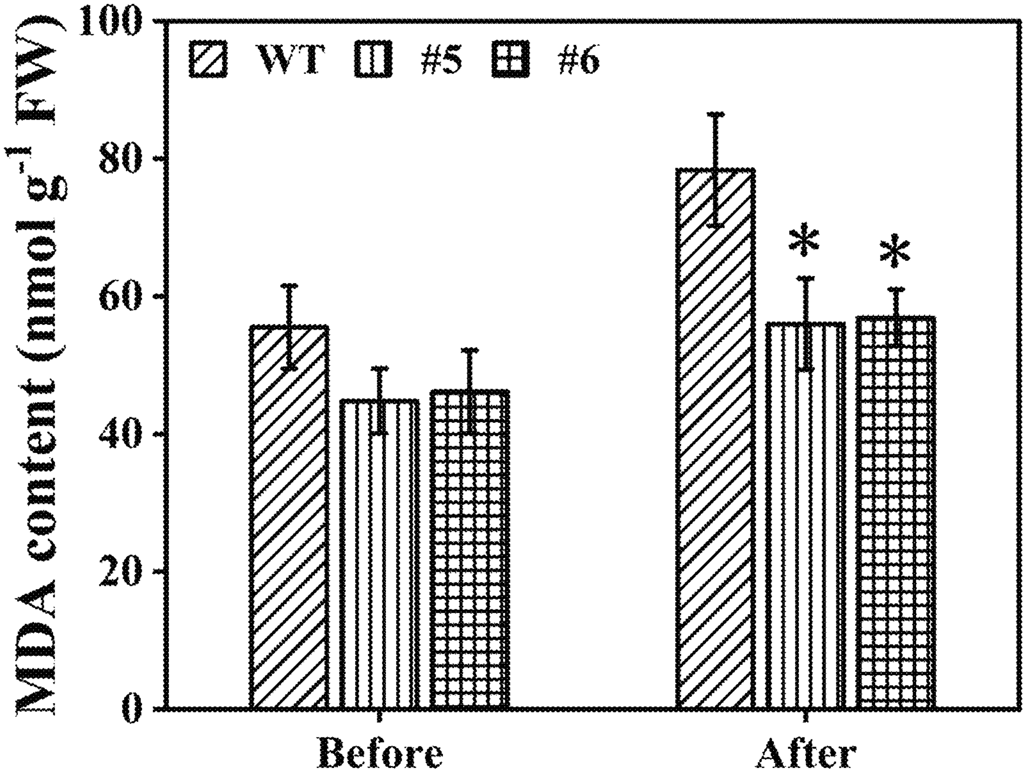
Figure 4F:
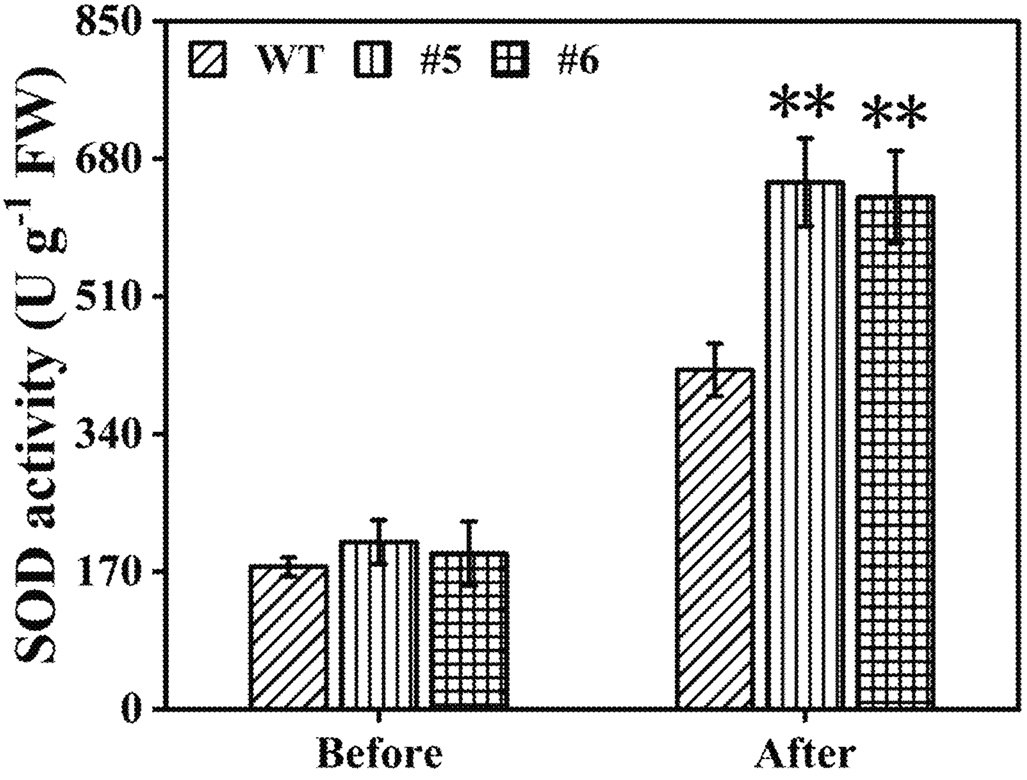
Figure 4G:
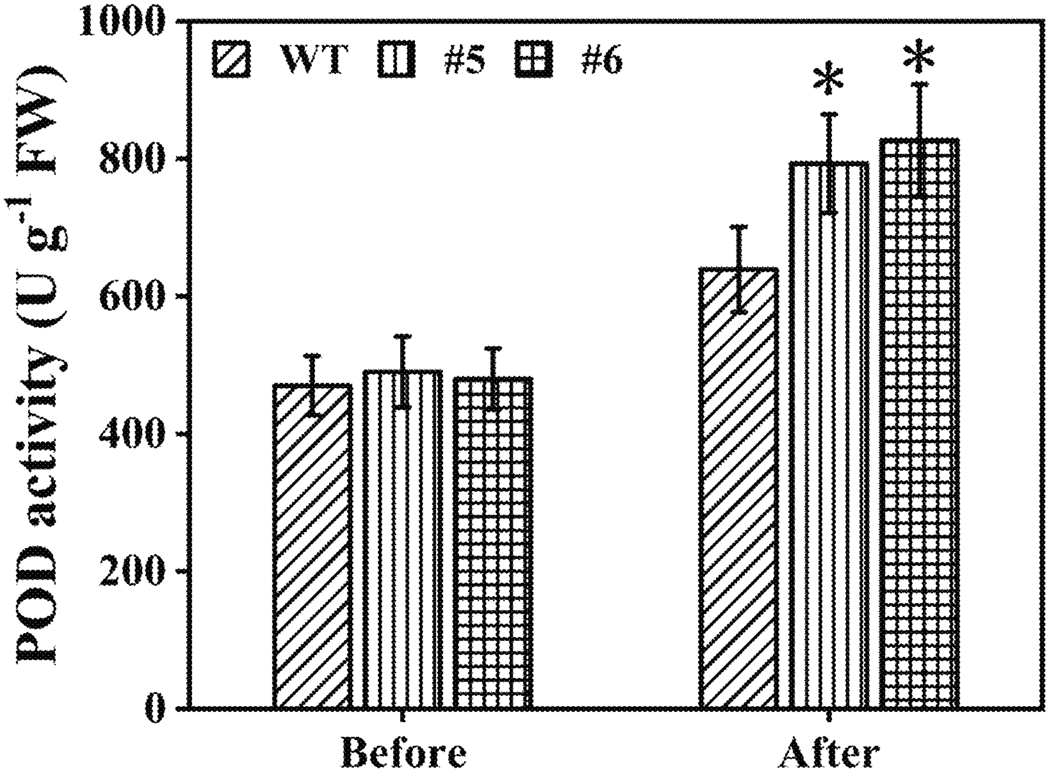
Figure 4H:
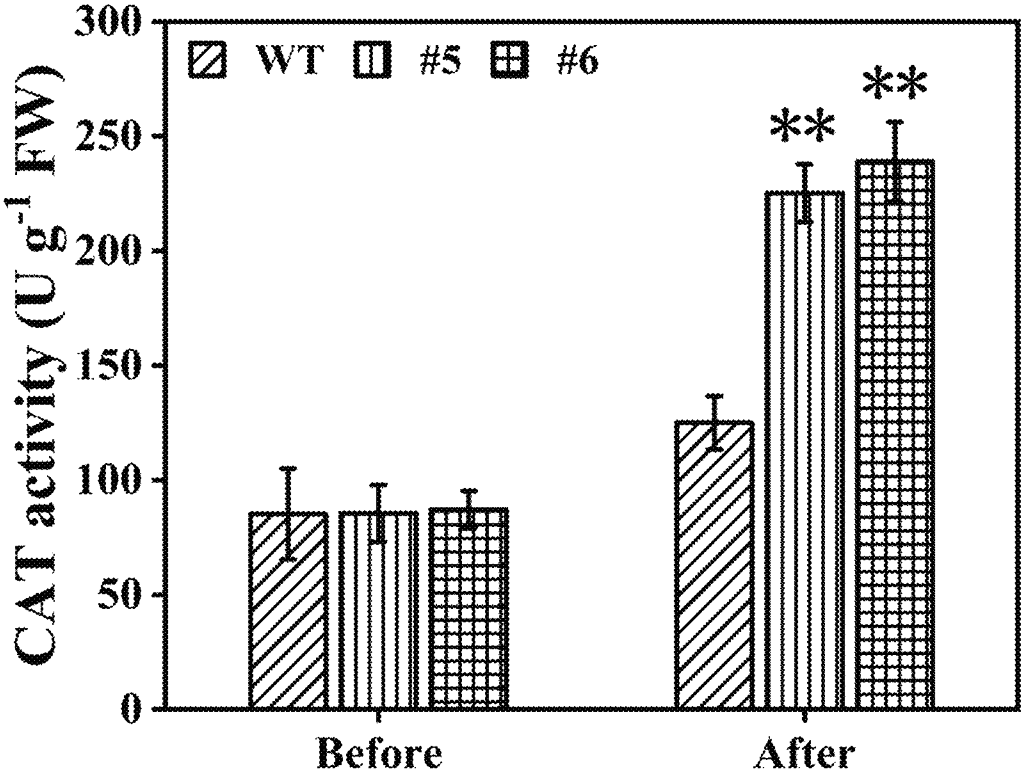

Before drought and high-salt stress treatments, there were no significant differences in the resistance physiological indicators between wild-type lemon (WT) and csi-miRn0008 silencing expression lemon lines (STTM-3 to STTM-6). After drought and high-salt stress treatments, the anti-superoxide anion activity of lemon leaves in the csi-miRn0008 silencing expression lemon lines was significantly higher than that of wild-type lemon (FIG. 3B, FIG. 4B); after drought and high-salt stress treatments, the maximum photosynthetic efficiency of lemon leaves in the csi-miRn0008 silencing expression lemon lines was extremely significantly higher than that of wild-type lemon (FIG. 3C, FIG. 4C), where the maximum photosynthetic efficiency is defined by the potential quantum yield of photosystem II (Ev/Em); after drought and high-salt stress treatments, the malondialdehyde (MDA) content and hydrogen peroxide ($H_2O_2$) content of leaves in the csi-miRn0008 silencing expression lemon lines were significantly ($0.01<P<0.05$) lower than those of wild-type lemon, while activities of the superoxide dismutase (SOD), peroxidase (POD), and catalase (CAT) were significantly higher than those of wild-type lemon (FIG. 3D to FIG. 3H, FIG. 4D to FIG. 4H). * represented the significance level ($p<0.05$); ** represented the extremely significant level ($p<0.01$).

In summary, the csi-miRn0008 silencing expression lemon lines showed stronger drought and salt resistance than the wild-type lemon.

The above descriptions are merely preferred embodiments of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. An expression vector, wherein the expression vector carries an expression cassette containing a csi-miRn0008 mimic target tandem sequence, and the csi-miRn0008 mimic target tandem sequence is set forth in SEQ ID NO: 4.

2. An engineered *Agrobacterium* strain, comprising the expression vector according to claim 1.

* * * * *

SEQUENCE LISTING

```
Sequence total quantity: 20
SEQ ID NO: 1           moltype = RNA  length = 21
FEATURE                Location/Qualifiers
source                 1..21
                       mol_type = other RNA
                       note = A mature sequence of csi-miRn0008
                       organism = synthetic construct
SEQUENCE: 1
cggaacggcg cggtgtccgc t                                              21

SEQ ID NO: 2           moltype = RNA  length = 302
FEATURE                Location/Qualifiers
source                 1..302
                       mol_type = other RNA
                       note = A precursor sequence of csi-miRn0008
                       organism = synthetic construct
SEQUENCE: 2
acacattggg gccaggacgc tgtccttcca caacttgaat atcatagtta tgaattacgc  60
cggcagccac agctttcatt tgagtgaaag cgacctcttt gcctaaacaa gtccttggtc  120
ctgcattaaa tgagaagaac ttgtacgacg gctcccattt gatccctcca ctttcagaaa  180
tccatctttc aggcctaaat tccaagcaat cttctcccca tattgacttc attctcccca  240
ttgcatacag agaaaacaag atctttgttc tcggaacggc gcggtgtccg cttggaagag  300
tg                                                                 302

SEQ ID NO: 3           moltype = DNA  length = 302
FEATURE                Location/Qualifiers
source                 1..302
                       mol_type = other DNA
                       note = A DNA molecule encoding the precursor sequence of
                        the csi-miRn0008
                       organism = synthetic construct
SEQUENCE: 3
acacattggg gccaggacgc tgtccttcca caacttgaat atcatagtta tgaattacgc  60
cggcagccac agctttcatt tgagtgaaag cgacctcttt gcctaaacaa gtccttggtc  120
ctgcattaaa tgagaagaac ttgtacgacg gctcccattt gatccctcca ctttcagaaa  180
tccatctttc aggcctaaat tccaagcaat cttctcccca tattgacttc attctcccca  240
ttgcatacag agaaaacaag atctttgttc tcggaacggc gcggtgtccg cttggaagag  300
tg                                                                 302

SEQ ID NO: 4           moltype = DNA  length = 140
FEATURE                Location/Qualifiers
source                 1..140
                       mol_type = other DNA
                       note = csi-miRn0008 mimic target tandem sequence
                       organism = synthetic construct
SEQUENCE: 4
atttggagag aacacgggat ccagcggaca ccgagtcgcc gttccggttg ttgttgttat  60
ggtctaattt aaatatggtc taaagaagaa gaatagcgga caccgagtcg ccgttccgga  120
gctcgaattt ccccgatcgt                                              140

SEQ ID NO: 5           moltype = DNA  length = 18
FEATURE                Location/Qualifiers
source                 1..18
                       mol_type = other DNA
                       note = Upstream primer Primer F of leaf DNA of Newhall
                        navel orange
                       organism = synthetic construct
SEQUENCE: 5
acacattggg gccaggac                                                 18

SEQ ID NO: 6           moltype = DNA  length = 18
FEATURE                Location/Qualifiers
source                 1..18
                       mol_type = other DNA
                       note = Downstream primer Primer R of leaf DNA of Newhall
                        navel orange
                       organism = synthetic construct
SEQUENCE: 6
cactcttcca agcggaca                                                 18

SEQ ID NO: 7           moltype = DNA  length = 32
```

```
FEATURE                Location/Qualifiers
source                 1..32
                       mol_type = other DNA
                       note = Upstream primer F-35S
                       organism = synthetic construct
SEQUENCE: 7
atgctctaga agattagcct tttcaatttc ag                          32

SEQ ID NO: 8           moltype = DNA  length = 31
FEATURE                Location/Qualifiers
source                 1..31
                       mol_type = other DNA
                       note = Downstream primer R-35S
                       organism = synthetic construct
SEQUENCE: 8
cgcggatccc gtgttctctc caaatgaaat g                           31

SEQ ID NO: 9           moltype = DNA  length = 19
FEATURE                Location/Qualifiers
source                 1..19
                       mol_type = other DNA
                       note = Upstream primer F-d35S
                       organism = synthetic construct
SEQUENCE: 9
tatgcttccg gctcgtatg                                         19

SEQ ID NO: 10          moltype = DNA  length = 19
FEATURE                Location/Qualifiers
source                 1..19
                       mol_type = other DNA
                       note = Downstream primer R-d35S
                       organism = synthetic construct
SEQUENCE: 10
atccagactg aatgcccac                                         19

SEQ ID NO: 11          moltype = DNA  length = 18
FEATURE                Location/Qualifiers
source                 1..18
                       mol_type = other DNA
                       note = Upstream primer M13-F
                       organism = synthetic construct
SEQUENCE: 11
tgtaaaacga cggccagt                                          18

SEQ ID NO: 12          moltype = DNA  length = 18
FEATURE                Location/Qualifiers
source                 1..18
                       mol_type = other DNA
                       note = Downstream primer M13-R
                       organism = synthetic construct
SEQUENCE: 12
caggaaacag ctatgacc                                          18

SEQ ID NO: 13          moltype = DNA  length = 21
FEATURE                Location/Qualifiers
source                 1..21
                       mol_type = other DNA
                       note = Upstream primer F-STTM
                       organism = synthetic construct
SEQUENCE: 13
atttggagag aacacgggat c                                      21

SEQ ID NO: 14          moltype = DNA  length = 18
FEATURE                Location/Qualifiers
source                 1..18
                       mol_type = other DNA
                       note = Downstream primer R-STTM
                       organism = synthetic construct
SEQUENCE: 14
cgatcgggga aattcgag                                          18

SEQ ID NO: 15          moltype = DNA  length = 22
FEATURE                Location/Qualifiers
source                 1..22
                       mol_type = other DNA
                       note = Upstream primer 35S-F
                       organism = synthetic construct
SEQUENCE: 15
taacagaact cgccgtaaag ac                                     22
```

-continued

```
SEQ ID NO: 16           moltype = DNA  length = 50
FEATURE                 Location/Qualifiers
source                  1..50
                        mol_type = other DNA
                        note = miRNA stem-loop primer
                        organism = synthetic construct
SEQUENCE: 16
gtcgtatcca gtgcagggtc cgaggtattc gcactggata cgacagcgga            50

SEQ ID NO: 17           moltype = DNA  length = 16
FEATURE                 Location/Qualifiers
source                  1..16
                        mol_type = other DNA
                        note = Upstream primer miRn0008-F
                        organism = synthetic construct
SEQUENCE: 17
gcggaacggc gcggtg                                                 16

SEQ ID NO: 18           moltype = DNA  length = 20
FEATURE                 Location/Qualifiers
source                  1..20
                        mol_type = other DNA
                        note = Downstream primer miRn0008-R
                        organism = synthetic construct
SEQUENCE: 18
agtgcagggt ccgaggtatt                                             20

SEQ ID NO: 19           moltype = DNA  length = 24
FEATURE                 Location/Qualifiers
source                  1..24
                        mol_type = other DNA
                        note = Upstream primer U6-F
                        organism = synthetic construct
SEQUENCE: 19
ttgggacgat acacagaaaa ttag                                        24

SEQ ID NO: 20           moltype = DNA  length = 23
FEATURE                 Location/Qualifiers
source                  1..23
                        mol_type = other DNA
                        note = Downstream primer U6-R
                        organism = synthetic construct
SEQUENCE: 20
gatttgtgcg tgtcattcct gtc                                         23
```